(12) United States Patent
Clarkin et al.

(10) Patent No.: US 8,216,980 B2
(45) Date of Patent: Jul. 10, 2012

(54) METHOD OF MAKING A MICRO-CHANNEL ARRAY DEVICE

(75) Inventors: James P. Clarkin, Scottsdale, AZ (US); Gary W. Nelson, Glendale, AZ (US); Robert J. Macomber, Phoenix, AZ (US)

(73) Assignee: Polymicro Technologies LLC, Phoenix, AZ (US)

( * ) Notice: Subject to any disclaimer, the term of this patent is extended or adjusted under 35 U.S.C. 154(b) by 1605 days.

(21) Appl. No.: 11/198,172

(22) Filed: Aug. 8, 2005

(65) Prior Publication Data
US 2005/0287047 A1    Dec. 29, 2005

Related U.S. Application Data

(63) Continuation of application No. 09/771,569, filed on Jan. 30, 2001, now abandoned.

(60) Provisional application No. 60/254,881, filed on Dec. 13, 2000.

(51) Int. Cl.
    *C40B 60/00* (2006.01)
(52) U.S. Cl. ........................................................ 506/33
(58) Field of Classification Search ........................ None
    See application file for complete search history.

(56) References Cited

U.S. PATENT DOCUMENTS

| | | | |
|---|---|---|---|
| 3,607,185 A | | 9/1971 | Andrysiak |
| 4,848,869 A | * | 7/1989 | Urruti ............................. 385/128 |
| 5,080,706 A | | 1/1992 | Snyder et al. |
| 5,173,097 A | * | 12/1992 | Jansen ............................. 65/403 |
| 5,176,881 A | | 1/1993 | Sepaniak et al. |
| 5,372,625 A | | 12/1994 | Brehm et al. |
| 5,429,734 A | | 7/1995 | Gajar et al. |
| 5,585,069 A | | 12/1996 | Zanzucchi et al. |
| 5,639,423 A | | 6/1997 | Northrup et al. |
| 5,681,484 A | | 10/1997 | Zanzucchi et al. |
| 5,802,236 A | * | 9/1998 | DiGiovanni et al. ......... 385/127 |
| 5,843,767 A | | 12/1998 | Beattie |
| 5,852,495 A | | 12/1998 | Parce |
| 5,867,327 A | | 2/1999 | Snyder |
| 5,904,824 A | | 5/1999 | Oh |
| 5,922,591 A | | 7/1999 | Anderson et al. |
| 6,066,020 A | | 5/2000 | Devoe et al. |

FOREIGN PATENT DOCUMENTS

| | | |
|---|---|---|
| GB | 2 189 480 | 10/1987 |
| JP | 5-196565 A | 8/1993 |
| JP | 5-240872 A | 9/1993 |
| JP | 6-10900 A | 1/1994 |
| JP | 2000-304686 A | 11/2000 |
| WO | 99/55460 | 11/1999 |

OTHER PUBLICATIONS

AMP, "Designers Guide to Fiber Optics," *AMP Incorporated*, Harrisburg, PA 17105, pp. 38-43.
Introductory Offer for HPCE '98, New Multi-Bore Capillary Columns for CE and CEC, UOP mat/sen Micro-Fabricated Capillary Structures.
Monro et al., "Holey Optical Fibers: An Efficient Modal Model," *Journal of Lightwave Technology*, vol. 17, No. 6, Jun. 1999, pp. 1093-1102.
New Multi-Bore Capillary Columns for CE and CEC from UOP mat/sen.
"Photonic Crystal Fibers," *Blazephotonics*, Highly Nonlinear Fiber.
"Photonic Crystal Fibers," *Blazephotonics*, Hollow Core Fiber.
"Photonic Crystal Fibers," *Blazephotonics*, Large-Core Endlessly Single-Mode Fiber.
Tonucci et al., "Nanochannel Array Glass," Science, vol. 258, No. 5083, Oct. 30, 1992, pp. 783-785.
Webster's II New Riverside University Dictionary, 1994, *Houghton Mifflin Company*, p. 248.
Office Action dated Jul. 27, 2007 corresponding to Japanese Patent Application No. 2002-549935.

* cited by examiner

*Primary Examiner* — Amber D. Steele
(74) *Attorney, Agent, or Firm* — Pillsbury Winthrop Shaw Pittman, LLP

(57) ABSTRACT

Micro channel array devices drawn from a bulk preform having an array of components to reduce the cross section. The reduced cross section fiber like structure is cut to produce individual arrays of small scale. End caps are drawn and optionally micro machined. The end caps are used to provide input and output ports and other structures for use with the micro channel arrays. A micro channel array may be used with different end caps for analysis and may form a lab on a chip or a component thereof.

33 Claims, 13 Drawing Sheets

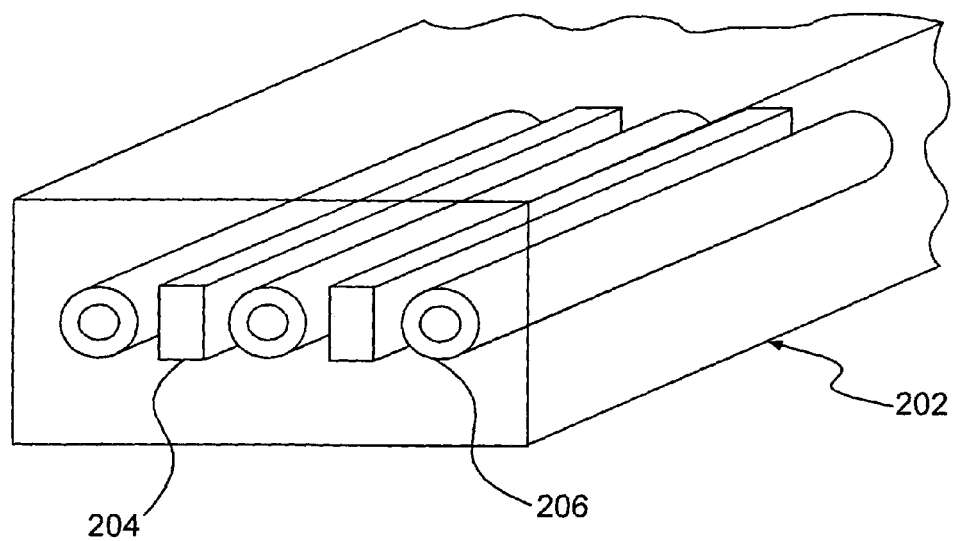
FIG. 14
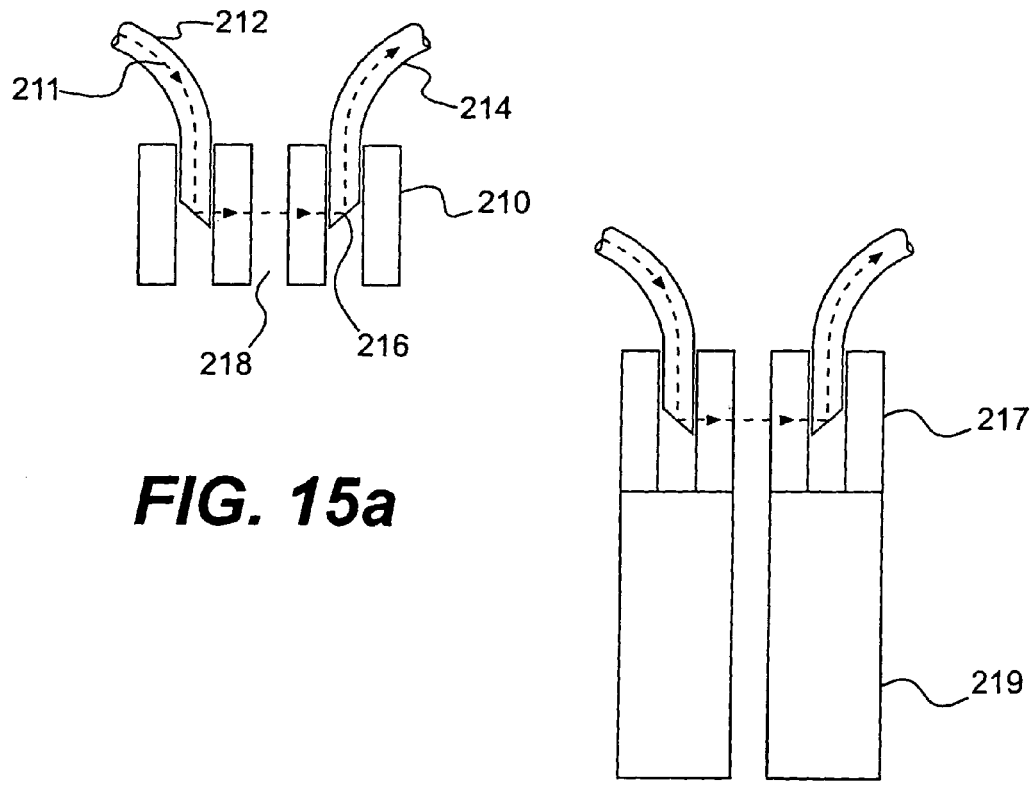
FIG. 15a
FIG. 15b

METHOD OF MAKING A MICRO-CHANNEL ARRAY DEVICE

This is a continuation of U.S. application Ser. No. 09/771,569, filed Jan. 30, 2001, which claims priority to U.S. Provisional Application No. 60/254,881, filed Dec. 13, 2000.

BACKGROUND OF THE INVENTION

1. Field of the Invention

The present invention relates generally to micro channel array structures. More particularly, the present invention relates to a device constructed by drawing a bulk preform to produce the micro channel array and a method of analysis utilizing such structures.

2. Background of the Invention

As the demand for rapid, accurate and inexpensive analytical techniques has grown, there has been a drive to develop smaller analytical devices. Such small devices can provide the ability to run hundreds or thousands of simultaneous experiments in a single laboratory, allowing heretofore impossible or impractical results to be achieved. For example, combinatorial chemists may now perform thousands of simultaneous syntheses using a fraction of the time and materials necessary to perform even one conventional synthesis. Pharmaceutical researchers, DNA analysts and a wide variety of other biologists and chemists have benefited from the revolution in lab on a chip technologies.

In order to make this possible, lab on a chip devices generally consist of microfluidic systems fabricated on a planar substrate. The substrate is generally selected according to the desired use and may be chosen to be resistant to acids, bases, salts, temperature extremes, temperature variations and/or applied electromagnetic fields. Further, the substrate should be relatively non-reactive with whatever chemicals might be used as part of the experiments to be performed. Examples of such substrates include glass, fused silica, quartz crystals, silicon, diamond and a variety of polymers. The substrate may be opaque or transparent, according to the application. For example, if optical detection is used to monitor the process, transparent substrates may be desirable to allow signal transmission.

In many cases, the lab on a chip may essentially consist of several channels in a surface or in the interior of the substrate. A typical channel may have a depth of about 10 μm and a width of about 60 μm.

Conventionally, lab on a chip devices have been manufactured using techniques similar to those used to fabricate microprocessors and other small scale electronic devices. For example it is common to use photolithography, chemical etching, plasma deposition, ion beam deposition, sputtering, chemical vapor deposition and other techniques commonly used in the semiconductor industry. Such techniques tend to be expensive and capital intensive. A single photolithography system can cost up to $20 million, not including the associated facilities such as clean rooms, vibration isolation structures and the like.

Moreover, photolithography has been unable to successfully produce channels with high aspect ratios or straight walls, has an inherently low production rate and generally uses materials which are of lower quality such as borosilicate glass or plastics.

In lieu of the above fabrication methods, micromachining techniques such as laser drilling, micro milling and the like or injection molding, microcasting or other casting techniques may be used. These techniques are generally slow and involve extremely high precision machining operations at the limit of current technologies.

In the manufacture of optical fibers, a pure silica tube has a doped silica layer deposited onto its interior surface by a process known as chemical vapor deposition. The tube is heated to cause it to collapse into a solid rod. The rod is heated and drawn to greatly increase its length and reduce its cross section, creating a flexible optical fiber.

For certain applications, a glass rod may be formed with pores therein prior to drawing to serve as a pipette, for example. The drawn fiber has tubes formed by the stretched pores. The tubes extend along the length of the fiber.

SUMMARY OF THE INVENTION

The present invention addresses the needs identified above by providing a micro channel array device produced by forming a preform body having channels therein, drawing the preform body to reduce a cross section thereof and to increase a length of the preform body to form an extended array, and cutting the extended array to a desired length.

Another embodiment of the present invention includes a method of analyzing by introducing a plurality of sample components to a drawn substrate having a length, the drawn substrate having at least two drawn channels formed therein. The drawn channels extend in a direction parallel to the length, the substrate includes inlets and outlets disposed in cooperating relation with the drawn channels Yet another embodiment of the present invention includes a device for analyzing a plurality of sample components, including a drawn substrate having a length, the drawn substrate having at least two drawn channels formed therein. The drawn channels extend in a direction parallel to the length. The device includes at least one endcap substrate having at least one endcap channel, the at least one endcap channel being in fluid communication with a selected one of the drawn channels, a plurality of the drawn channels, and/or another endcap channel.

The device may be employed in a lab on a chip device.

Another aspect of the present invention includes a drawn substrate manufactured by a process including providing a preform body having at least one channel and at least one optical waveguide preform therein and extending along a length of the preform body, drawing the preform body to extend the length thereof such that a length of the at least one channel is extended while substantially maintaining a cross sectional geometry of the at least one channel and such that a length of the at least one optical waveguide preform is extended while substantially maintaining a cross sectional geometry of the at least one optical waveguide preform, and cutting the drawn preform body to a desired length.

BRIEF DESCRIPTION OF THE DRAWINGS

The accompanying drawings, which are incorporated in and constitute a part of this specification illustrate embodiments of the invention and together with the description, explain the objects, advantages, and principles of the invention.

FIG. 14 shows an example of a drawn micro channel array structure having integrated drawn optical waveguides according to the present invention.

FIG. 15a-b shows a side view examples of a drawn micro channel array device having integrated optical fibers, according to the present invention.

DETAILED DESCRIPTION OF THE PREFERRED EMBODIMENTS

Figure 1:
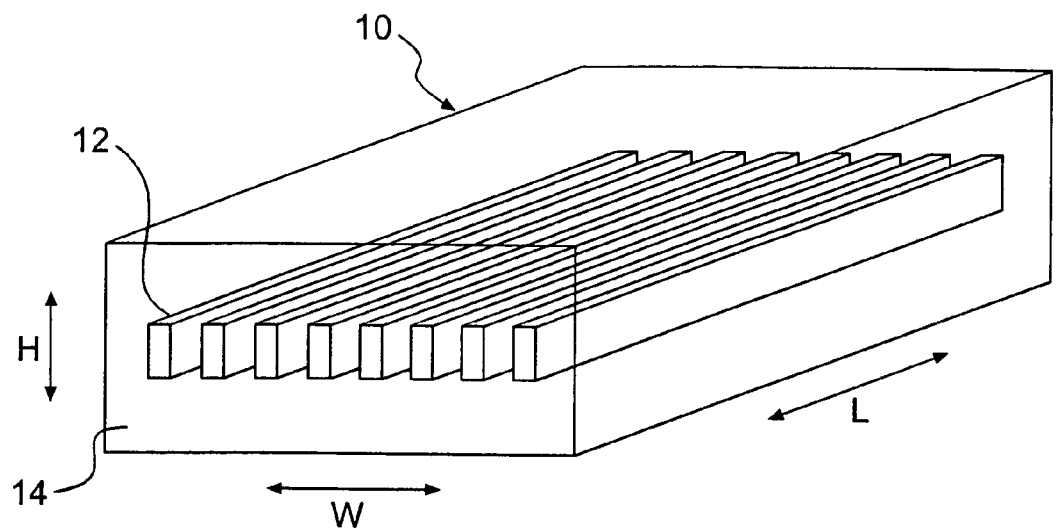
FIG. 1 shows an example of a drawn substrate according to the present invention.

In the following description, for purposes of explanation and not limitation, specific details are set forth such as particular components, techniques, etc. in order to provide a thorough understanding of the present invention. However, the invention may be practiced in other embodiments that depart from these specific details. In some instances, detailed descriptions of well-known devices may be omitted so as not to obscure the description of the present invention with unnecessary details.

The following definitions are used herein:

Drawn micro channel array devices: a complete structure consisting of any of drawn channels, endcaps, optical waveguides, optical fibers, lenses, reflectors, and portals.

Draw process: the process whereby a substrate in the form of a block or rod is drawn, usually while being heated, stretching it along its length and reducing the cross sectional area to a desired size.

Preform body: the initial substrate with machined or otherwise formed channels prior to having its cross sectional area reduced by the draw process. The preform body may have an optical waveguide embedded therein.

Channels: the channels in the substrate prior to drawing.

Drawn substrate: the body of material drawn from the preform body.

Drawn channels: the channels within the drawn substrate.

Endcap substrate: the body of material which is attached to either drawn substrates or other endcaps to enhance the function of the drawn micro channel array devices. The endcap substrates contain portals, mixing chambers, fluid conduits, and other structures used in the analysis technique.

Endcap channels: the channels within the endcap substrate.

Ports, outlets and portals: additional openings other than the channels machined or otherwise formed in either a channel substrate or endcap substrate. These ports put the drawn channels and endcap channels in fluid communication with interfaces outside the drawn substrate and endcap substrate. The ports generally connect to the channels at an angle between 1 and 90 degrees from the channel itself.

Fluid communication: condition where conduits are sufficiently connected to allow fluid to flow there through.

Conduit: any of drawn channel, endcap channel, or portal.

Cross sectional geometry: a shape of a preform body, drawn substrate, or endcap substrate if viewed axially down its length. Includes similar geometric figures, that is figures with the same shape but of a differing scale.

Optical waveguide preform: an initial optical waveguide in its bulk form prior to having its cross sectional area reduced by the draw process. This would be embedded in the above preform body, and drawn simultaneously with the channels.

Drawn optical waveguide: the optical waveguide after undergoing the draw process.

Reflector: a shape on an exterior surface of the drawn substrate or endcap substrate or on an interior surface of a channel that is designed such that light will reflect back into the substrate or channel within the substrate. The reflector would typically be coated with a reflective coating, including but not limited to silver.

Exterior wall: the exterior surface of either a drawn substrate or endcap substrate.

Interior wall: the interior surface of either a drawn substrate or endcap substrate which forms the defining edge of the drawn channel or endcap channel respectively.

Channel spacing: the distance between channels in either the drawn substrate or endcap substrate.

Rotational alignment: the alignment of channels in respect to other channels when rotated on the axis of the length. This can apply to either drawn channels or endcap channels.

Angular alignment: the alignment of channels in respect to other channels when rotated radially to the length. This can apply to either drawn channels or endcap channels.

Alignment Groove: A groove or protrusion from the surface of the drawn substrate or endcap substrate which allows for mechanical alignment of electrodes, optical fibers, lenses, detectors, transmitters, wires or other micro electromechanical devices to the drawn channels.

Optical Isolator: A region of material which filters out desired wavelengths of light such that selected drawn channels or other regions of the drawn substrate or drawn endcaps are optically isolated from other channels, regions, or external areas.

Optical Fiber: A separately drawn optical fiber which is inserted into or attached to the drawn micro channel array devices.

Detection: The quantification of the amount of analyte in a drawn channel or endcap channel at a particular location within one of those channels.

Referring now to FIG. 1, a drawn substrate 10 according to the present invention is shown. A series of drawn channels 12 is arrayed across a face 14 of the drawn substrate 10. In this example, the drawn substrate 10 is about 10 cm in length (L), about 1000 µm in height (H), and about 1500 µm in width (W). Each individual drawn channel 12 is about 50 µm in width and about 150 µm in height.

In general, it is preferable to create arrays of channels having a cross sectional area in the range of 0.0001 mm$^2$ to 1 mm$^2$, preferably 0.0025 mm$^2$ to 0.25 mm$^2$, and most preferably 0.005 mm$^2$ to 0.025 mm$^2$.

To form this array, a preform body is made, having similar proportions but of a larger size. The preform body contains channels which correspond to the drawn channels. The preform body is heated in a furnace and drawn, stretching it along its length and reducing the cross sectional area to the desired size while maintaining its geometry, that is the final, drawn substrate cross section is geometrically similar to the cross section of the original preform body, differing essentially only in size. By controlling the speed of the draw, the resulting cross sectional area can be controlled allowing formation of structures such as tapers. Preferably, a thickness monitor is provided. The thickness monitor supplies a control signal to the drawing process, so that a constant or appropriately varying cross section can be produced.

Though the drawn array does not require any coating, a protective coating can be applied over the drawn array as is done for optical fibers. Various coatings may be applied, according to the intended use. Materials for a coating may be selected, for example, from polyimide, acrylate, fluorinated acrylate, silicone, metal or optical cladding. It may be desirable to make use of multiple coatings or multiple layers of a single coating. If necessary, the coating can then be cured in a curing oven. If the coating is selected to have a lower index of refraction than the drawn substrate, the drawn substrate can act as a light guide. In the case that the drawn array is flexible, it may be coiled onto a take-up drum.

The preform body from which the drawn substrate is to be formed may be made from a variety of materials including, for example, glass, thermoplastic polymers, and ceramics In many cases, the preferred materials will be fused silica or quartz. These materials provide high strength, good transmission of light, including UV wavelengths, high degree of homogeneity and low fluorescence. Additionally, since such materials are commonly used for manufacture of drawn optical components, their behavior when heated and drawn is reasonably well understood.

Figure 2:
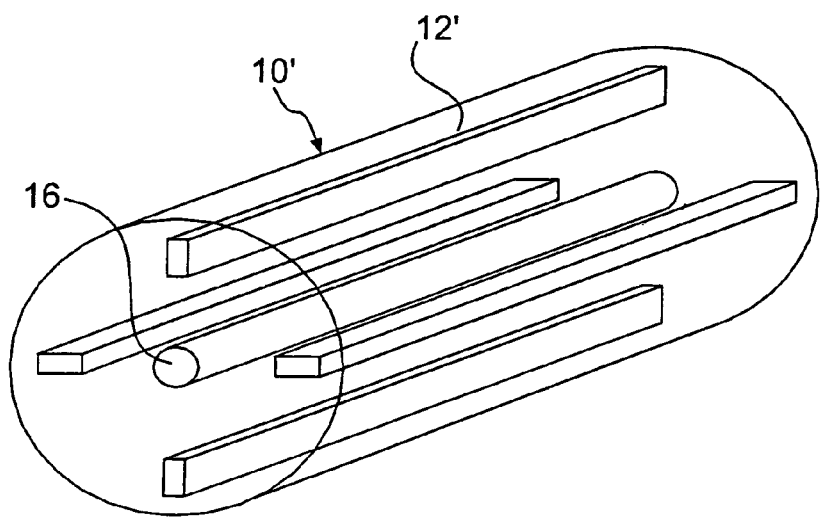
FIG. 2 shows an example of another drawn substrate according to the present invention.

An alternate drawn substrate 10' is shown in FIG. 2. The drawn substrate 10' of FIG. 2 has an annular array of drawn channels 12' of similar dimensions to the drawn channels 12 of FIG. 1. Additionally a central through hole 16 is provided. The central through hole 16 may be used to accommodate mechanical connectors, to allow a light signal to be injected into the hole, to allow a light signal to be transmitted from the hole, or to allow passage of a material from one end of the drawn substrate to the other.

Figure 3A:
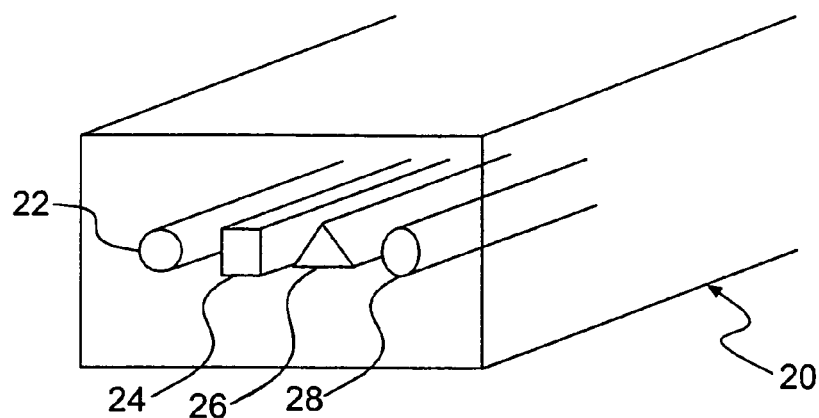
FIG. 3a shows an example of a drawn substrate incorporating a variety of drawn channel shapes according to the present invention.
Figure 3B:
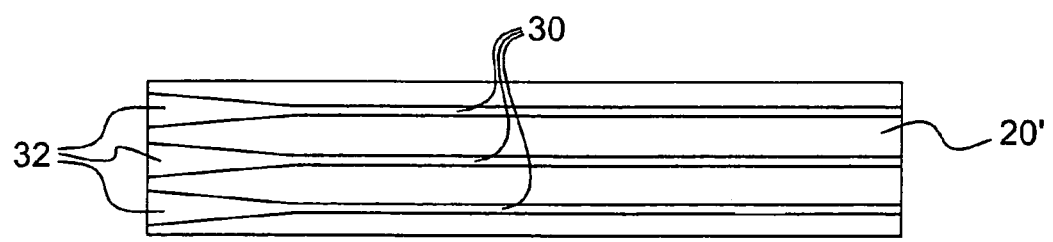
FIG. 3b shows an example of a micro channel array having tapered channels according to the present invention.

In FIG. 3a, a drawn substrate 20 is shown, illustrating several possible drawn channel shapes. A round channel 22, a rectangular channel 24, a triangular channel 26 and an oval channel 28 are shown. FIG. 3b shows an example of a drawn substrate 20' having drawn channels 30 with tapered portions 32. The tapered portions can be formed by varying various draw parameters including the rate of drawing, the draw tension, the draw temperature and the draw pressure during production of the drawn substrate. It may be necessary to machine the drawn substrate after the draw process in order to produce a desired exterior cross section while providing varying drawn channel cross sections. FIGS. 4a-j, likewise illustrate exemplary drawn channel and drawn substrate cross sections. A given drawn substrate may employ identical cross sectioned drawn channels as shown in FIG. 1, or, as shown in FIG. 3, a variety of cross sections.

Figure 4A:
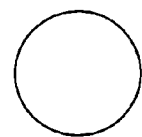
FIGS. 4a-j show examples of several drawn channel cross sections according to the present invention.
Figure 4B:
Figure 4C:
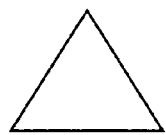
Figure 4D:
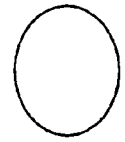
Figure 4E:
Figure 4F:
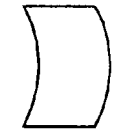
Figure 4G:
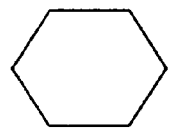
Figure 4H:
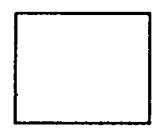
Figure 4I:
Figure 4J:
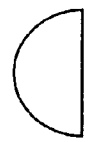

An interior or exterior wall may be adapted to act as a lens. That is the cross sectional shape of a drawn channel or drawn substrate is selected such that at least one wall forms a lens. For example, FIG. 4f shows a channel having a convex lens on one side and a concave lens on the other. This may be particularly useful in the case that an optical detector is employed. The curvature of the wall is selected to provide the appropriate focus or defocus of light passing through the wall. In contrast, a straight wall will produce minimal lensing effect, if any. The shape of the drawn channel may likewise be selected to maximize the sample volume or to alter the speed at which liquids flow through the drawn channel, for example. Likewise, a portion of the interior or exterior wall may act as a reflector. A particular shape may be selected to increase the reflectivity of the wall. However, in order to increase the reflectance of the wall over that caused by a change in index of refraction, the wall is preferably coated with a reflective coating, including but not limited to silver.

FIG. 5a-e show a series of end cap substrates for use with the drawn substrate. The end cap substrates can incorporate end cap channels, portals designed to provide fluidic communication with the drawn channels. The end caps substrates may include micro structures such as valves, switches, portals, mixing chambers or any other structures resulting in a lab on a chip device. Moreover, the end caps substrates may be terminal structures or may be used as an interface between a drawn micro channel array devices and the analytical instrument, as shown in the non-limiting examples illustrated in FIGS. 7-10, 17 and 18, and described below.

Figure 5A:
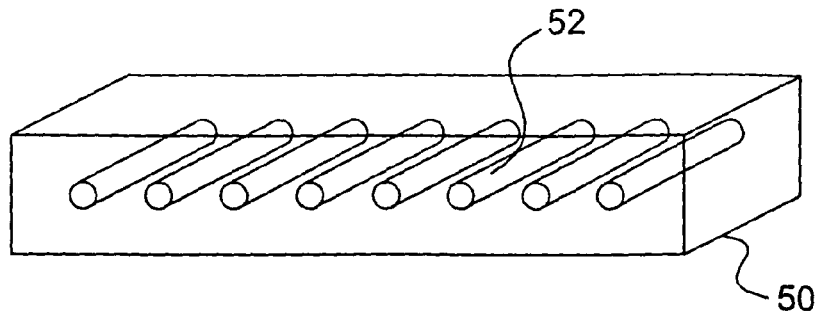
FIGS. 5a-e show examples of various endcap substrates and endcap channels configurations according to the present invention.
Figure 5B:
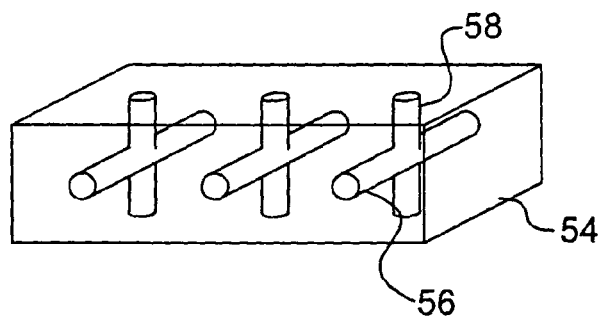
Figure 5C:
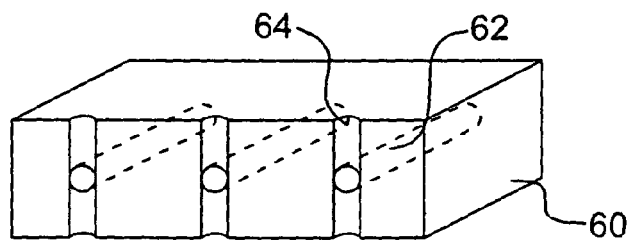
Figure 5D:
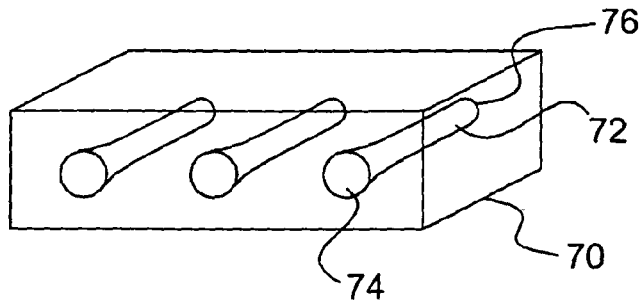
Figure 5E:
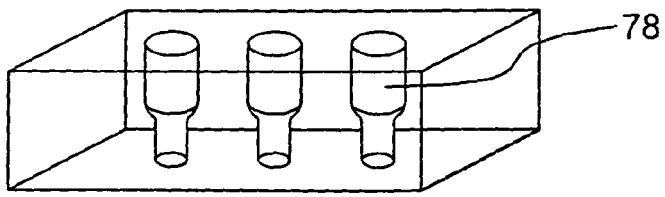

FIG. 5a shows an end cap substrate 50 which simply includes eight straight, round endcap channels 52. An end cap of this type may be manufactured in the same manner as the drawn substrate itself, and cut to the desired length. FIG. 5b shows an end cap substrate 54 with three endcap channels 56. Each channel 56 further incorporates side ports 58. While the end cap substrates 54 and channels 56 can be made through the drawing process, the side ports 58 require an additional machining step since they are, for example, perpendicular to the direction of draw. Similarly, FIG. 5c shows an end cap substrate 60 with three endcap channels 62 and side ports or channels 64 which may be machined into the end cap substrate 60. Unlike the side ports 58 as shown in FIG. 5b, the channels 64 of FIG. 5c are at the surface of the end cap substrate 60 and thus each channel 64 forms a semicircular trough. FIG. 5d shows an end cap substrate 70 having three endcap channels 72. Each channel 72 is tapered so that one end 74 is larger in diameter than the other end 76. To produce a tapered port 72, the tapered, or otherwise shaped, port may be formed by using a varied draw rate, mechanical machining, laser machining, or chemical etching. In order to create the end cap substrate 70 as shown, with tapered ports, but with a uniform external cross section, the exterior may have to be machined. FIG. 5e shows a similar endcap with a larger volume taper 78 which may serve as a capillary, pipette or as a reservoir. The endcap of FIG. 5e can be formed, for example as two constant cross sections joined by a taper.

Figure 6A:
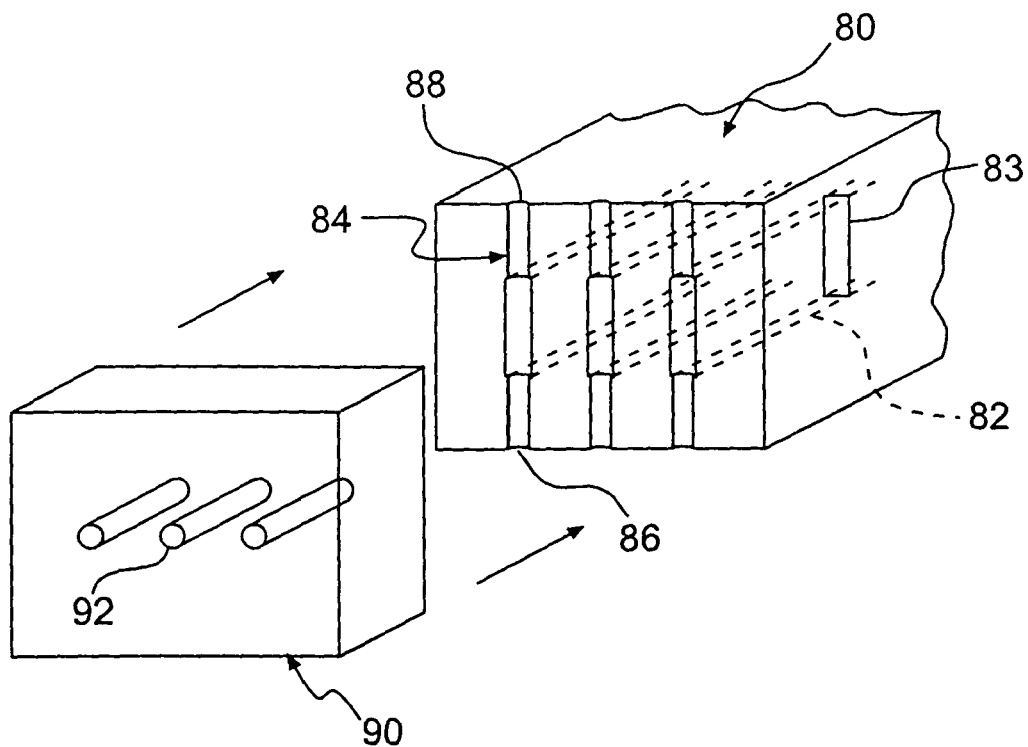
FIGS. 6a and 6b show examples of drawn micro channel array devices according to the present invention.
Figure 6B:
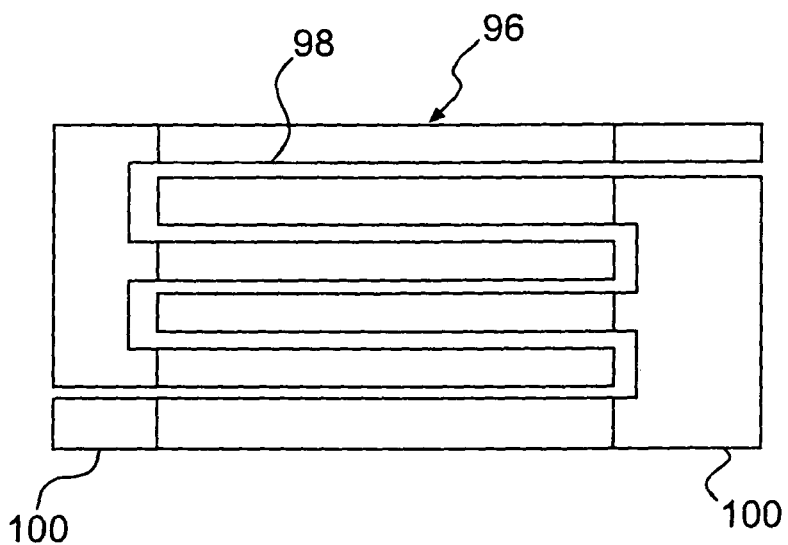

FIGS. 6a and 6b show how an end cap substrate may be used in conjunction with a drawn substrate to produce a complete micro channel array device. In FIG. 6a, a drawn substrate 80 contains three drawn channels 82, in this case, having a rectangular cross sectional geometry. A section 83 of one of the channels 82 is shown for illustrative purposes. At the end of each drawn channel 82, a machined transverse channel 84 is provided. In a particular application, one end 86 of each transverse channel can be used as a waste port, while the other end 88 acts as an analyte port. An end cap substrate 90 includes three channels 92 which are aligned with a central portion of the drawn channels 82 of the drawn substrate 80. The three channels 92 of the end cap substrate 90 act as buffer ports and are in fluid communication with the buffer port 88, the waste port 86, and the drawn channel 83 of the drawn substrate 80. The end cap substrate 90 and drawn substrate 80 are connected by any appropriate method including fusing and adhesive bonding. Since the end cap substrate 90 and drawn substrate 80 are similar in material and structure to optical fibers, many of the splicing techniques used in that field may be employed in the present invention.

End caps substrates and endcap channels may also be used to provide flexibility in drawn channel path length as shown in FIG. 6b. A drawn substrate 96 having several drawn channels 98 may be, for example, approximately 20 cm long. In some applications, such as capillary electrophoresis, it may be desirable to use a capillary having a length of 100 cm. By use of an end cap substrate 100 on each end which redirects flow along adjacent drawn channels 98, five 20 cm drawn channels may provide the desired 100 cm length. Moreover, the same drawn substrate 96 may be used to create, for example, two 40 cm drawn channels or one 40 cm and one 60 cm drawn channel by providing different end cap substrates 100.

Figure 7:
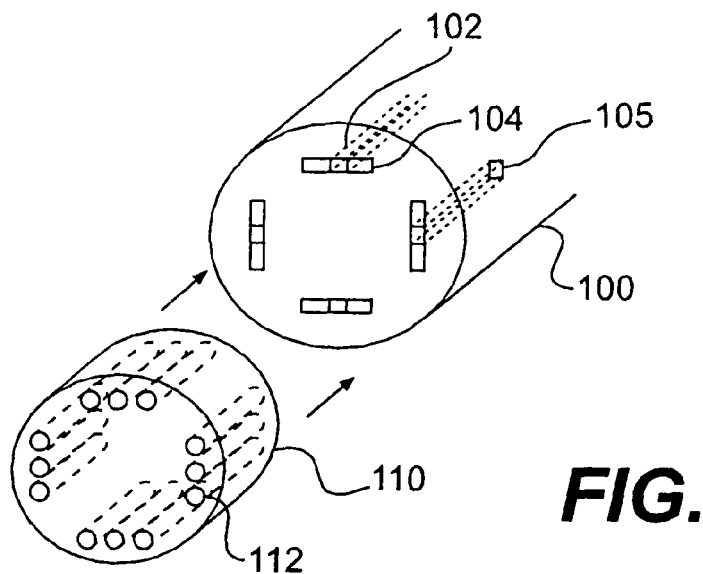
FIG. 7 shows an example of drawn micro channel array devices according to the present invention.

FIG. 7 shows a second end cap and drawn substrate combination. Drawn substrate 100 incorporates four drawn channels 102, radially arrayed about a central axis. Each drawn channel 102 has an associated conduit 104 which may be machined or otherwise formed in the end 106 of the drawn substrate 100. For illustrative purposes, a section 105 of one of the channels is shown. An end cap substrate 110 has four groups of three endcap channels 112 which may be machined or formed in a drawn end cap as discussed above. In one application, the endcap channels 112 act as ports, allowing transport of material into the channels 102.

Figure 8:
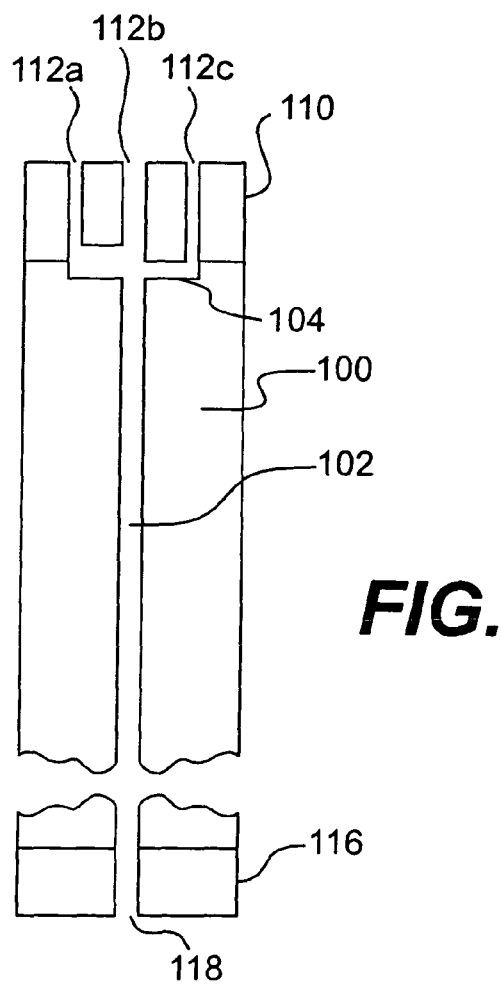
FIG. 8 shows a partial side view of a drawn micro channel array device and end cap of FIG. 7.
Figure 9:
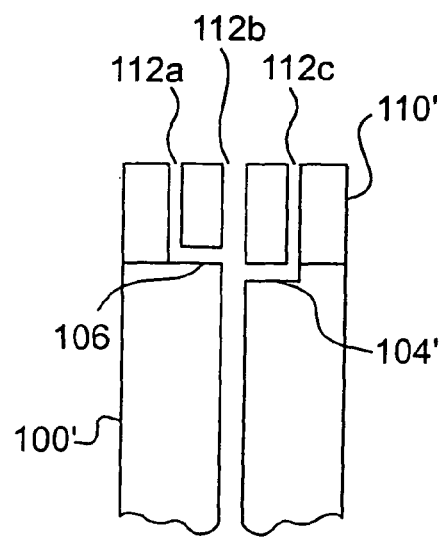
FIG. 9 shows an alternate partial side view of a drawn micro channel array device of FIG. 7.

FIGS. 8 and 9 show two alternate partial side views of the drawn micro channel array device of FIG. 7. In FIG. 8, the drawn substrate 100 is shown with one of the drawn channels 102 and one of the conduits 104. On one end is an end cap substrate 110, with three endcap channels 112a-c. The first channel 112a may be, for example, a buffer port, the second channel 112b, may be an analyte port while the third channel 112c may be a waste port. On the other end, a second end cap substrate 116 is provided with a through hole 118 corresponding to each drawn channel 102. In an alternate arrangement, shown in FIG. 9, the drawn substrate 100' contains only one portion of the conduit 104'. The other portion 106 is instead formed in the end cap substrate 110'. This is meant to demonstrate that the conduit can be machined or otherwise formed in either the endcap substrate or drawn substrate.

Figure 10:
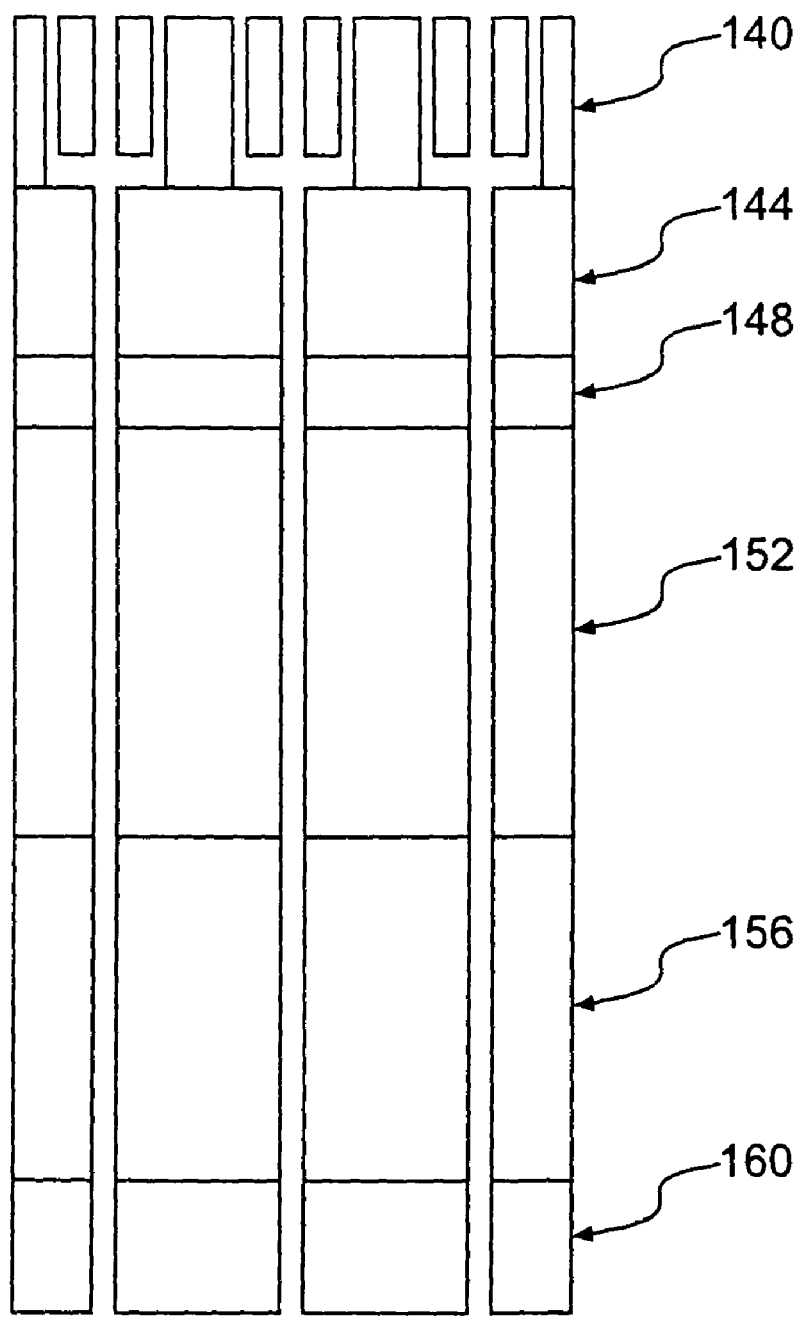
FIG. 10 shows an example of a multi-part drawn micro channel array devices in a lab on a chip structure according to the present invention.

As shown in FIG. 10, a more complicated drawn micro channel array device can be assembled from the basic parts. In the description of FIG. 10, the components are described without reference to the subsystems such as the actual channels, ports, slots and the like. Adjacent components are attached by fusing or bonding as appropriate.

An end cap substrate 140 acts as an interface to the analytical instrument section and contains ports and valves or valve regions. Next is a segment of drawn substrate 144 which contains drawn channels which act as mixing chambers. The mixing chambers lead into another end cap unit 148 which contains further valves. The valve section 148 controls fluids as they enter the capillary electrophoresis (CE) section 152. The capillary electrophoresis section includes drawn channels which act as capillaries for the CE process. The results of the CE process are read out by the detector section 156 which is preferably an end cap substrate which interfaces optically with the analytical instrument. Finally, another end cap substrate 160 contains output and/or waste outlet structures and interfaces again to the analytical instrument. As is apparent from FIG. 10, a variety of structures may be built in similar fashion with various combinations of end cap substrates and drawn substrate.

Figure 11:
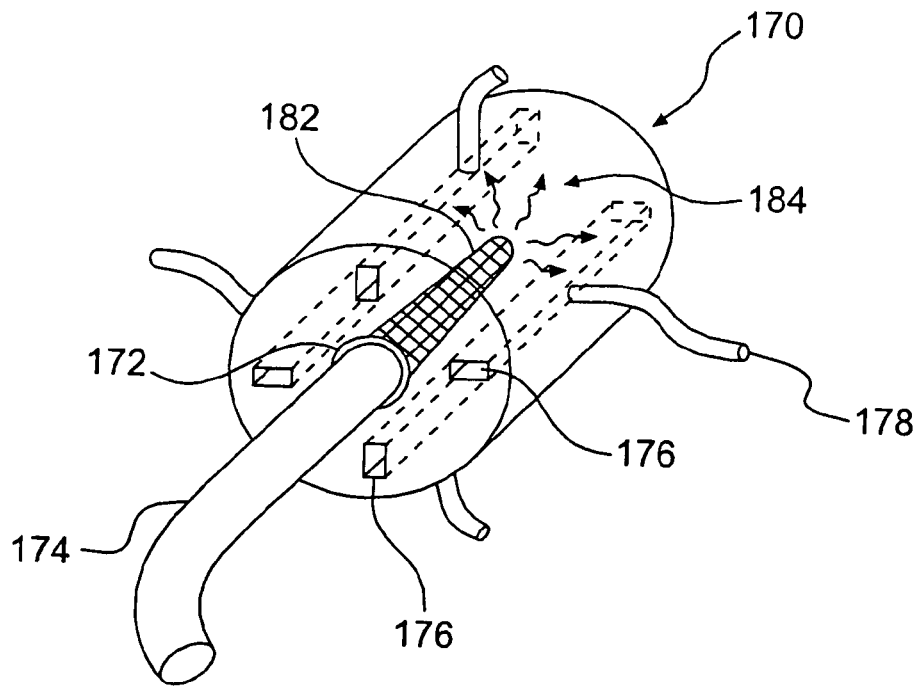
FIG. 11 shows another partial side view of a drawn micro channel array device having an integrated optical fiber according to the present invention.

Optical fibers may be integrated with drawn micro channel array devices in a variety of ways. As shown in FIG. 11, a drawn micro channel array device 170 having a central drawn channel 172 is suited to accept an optical fiber 174 within the channel 172. Arrayed around the optical fiber 174 are four drawn channels 176, each optically connected to an optical fiber 178. The optical fibers 178 are attached to one or more detectors, not shown. The detectors may be any suitable light detector such as a photodiode, scintillator, thermodetector, photoelectric detector, pyroelectric detector, photomultiplier, phosphor screen, photoconductive detector, etc. As shown, the optical fiber 174 includes a radially emitting tip 182. Photons 184 emitted from the tip 182 pass through the channels 176. In one application, if the channels contain a substance which fluoresces, the detector fibers 178 will carry the fluorescent light to the detectors. In an alternate application, the channels may be tested for a substance which blocks the photons from the tip 182. In the presence of a signal from the detector fibers 178, the substance is absent. Other uses for this device may be apparent to those skilled in the art.

In manufacturing the device of FIG. 11, the drawn micro channel array device 170 is first manufactured according to the method described above. The central channel 172 may either be formed integrally with the device 170, or may be later machined into the device 170. The detector optical fibers 178 are later added and are connecting by fusion splicing, mechanical coupling, or adhesives as appropriate.

Figure 12:
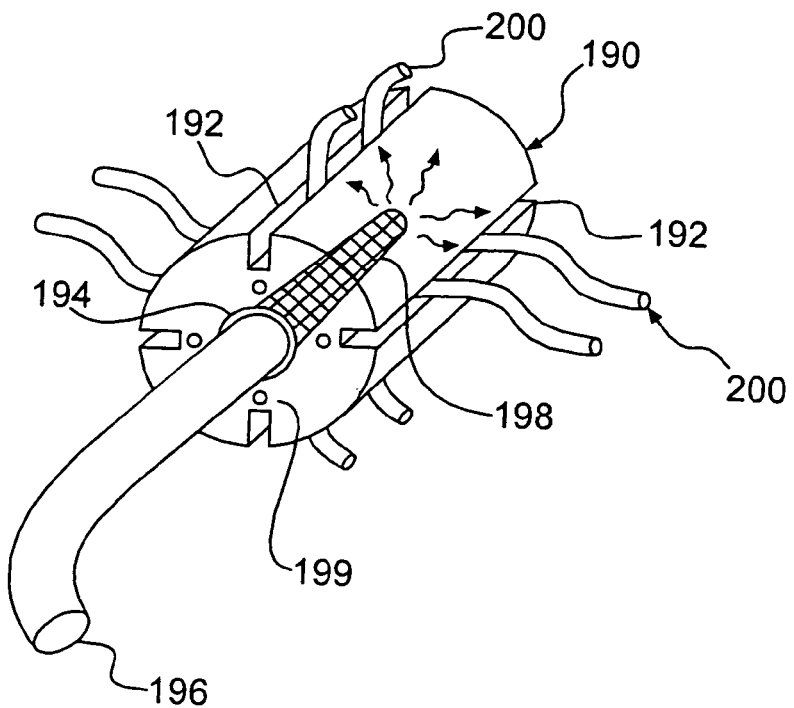
FIG. 12 shows an example of another drawn micro channel array devices having an integrated optical fiber according to the present invention.

A similar arrangement to that of FIG. 11 is shown in FIG. 12. In this device, a device 190 has several drawn or machined channels 192 at its surface. A central channel 194 again provides access for a source optical fiber 196 with an emitting tip 198. Arrayed around the optical fiber 196 are four drawn channels 199, each optically connected to an optical fiber 200. Several detector optical fibers 200 are arrayed within the channels 192 to transmit signals from the device to detectors, not shown. The channels at the surface act as a mechanical alignment and connection mechanism of the optical fibers 200 to the device 190.

Figure 13A:
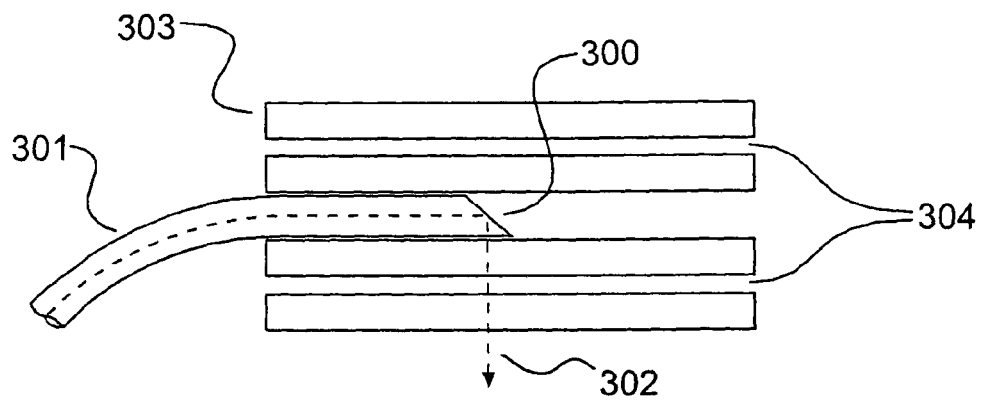
FIG. 13a-c shows examples of the means by which the light can be redirected from the axis of the fiber into or out of the micro channel array device.
Figure 13B:
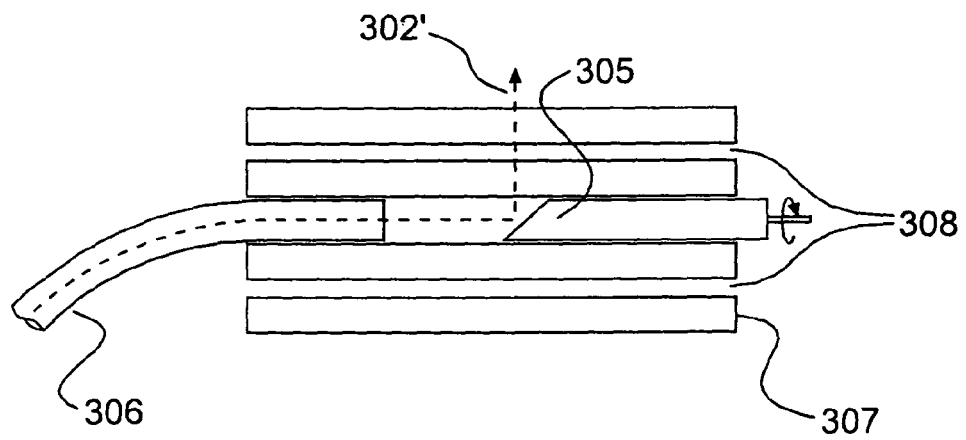
Figure 13C:
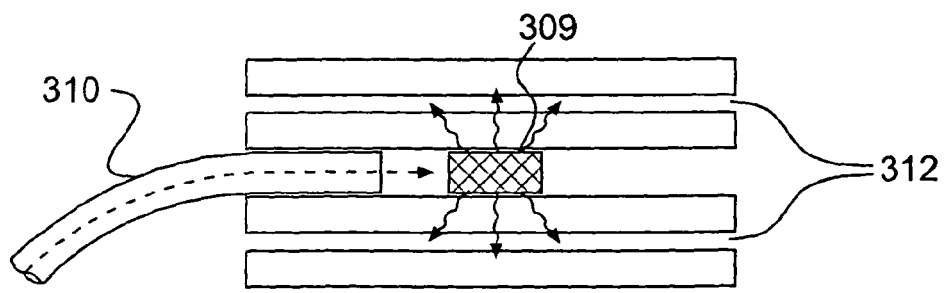

FIGS. 13a-c show three examples of how the photons 184 of FIG. 11 can be redirected. In FIG. 13a, an angled end 300 on the optical fiber 301 acts as a side fire device, directing the photons 302 at an angle to the fiber axis (typically 90 degrees). The optical fiber or device 303 can be rotated with respect to each other, thereby selecting the drawn channels 304 individually for analysis.

FIG. 13b shows another device similar to FIG. 13a, only in this case a reflector 305, separate from the optical fiber 301 is provided for redirecting the light. The reflector is rotatable with respect to the optical fiber 306 and device 307. The rotation allows selection of drawn channels 308 to be analyzed.

FIG. 13c shows another device similar to FIG. 13a, having as a structure for redirecting light a scattering medium 309, inserted in the central hole. The light is delivered to the device via the optical fiber 310 and the beam of photons is directed toward the scattering medium 309 which scatters the photons towards the drawn channels 312. Though the scattering medium 309 is shown to scatter in all directions, it could be arranged to scatter preferentially in one direction and be rotatable to select a given output channel as with the reflectors. Likewise, the reflectors and scattering medium could be replaced with any structure for redirecting light such as, for example, a diffractive optical element.

Referring now to FIG. 14, an drawn substrate 202 is shown with drawn channels 204 alongside drawn optical waveguides 206 embedded in the drawn substrate. This drawn substrate 202 may be formed by first creating a preform body, not shown. The preform body contains both channels 204, an embedded optical waveguide made of a similar material. The waveguide is formed by either a rod of lower refractive index than the surrounding preform body, or a rod which itself includes a central area of lower refractive index than an outer area on the rod. This difference in refractive index is necessary to achieve the condition of total internal reflection for waveguiding of the light. By drawing the preform body, the embedded optical waveguides are extended, forming drawn optical waveguides 206 and the channels are extended, forming drawn channels 204.

FIG. 15a provides a side view of an end cap substrate 210 which may be used as a detector device. A pair of optical fibers 212, 214 are disposed within the end cap substrate 210 and have end surfaces 216 which are machined to present a 45° angle. Light 211 enters the first fiber 212, is reflected off the surface 216 and is directed through a window portion of an endcap channel 218. Light exiting or emitted from the endcap channel is reflected off the end surface 216 and is then directed down fiber 214 and exits fiber 214 to the analytical instrument, not shown. The endcap channel 218 transports the analyte past the window between optical fibers 212 and 214, where it is optically analyzed. FIG. 15a may be applied as shown in FIGS. 13a-c and FIG. 15b wherein the 15a device is attached to a drawn substrate 219. The drawn substrate contains drawn channels where the analyte undergoes a CE process, for example, and subsequently travels into device 217 where it undergoes optical analysis, as is done in a CE separation.

Figure 16:
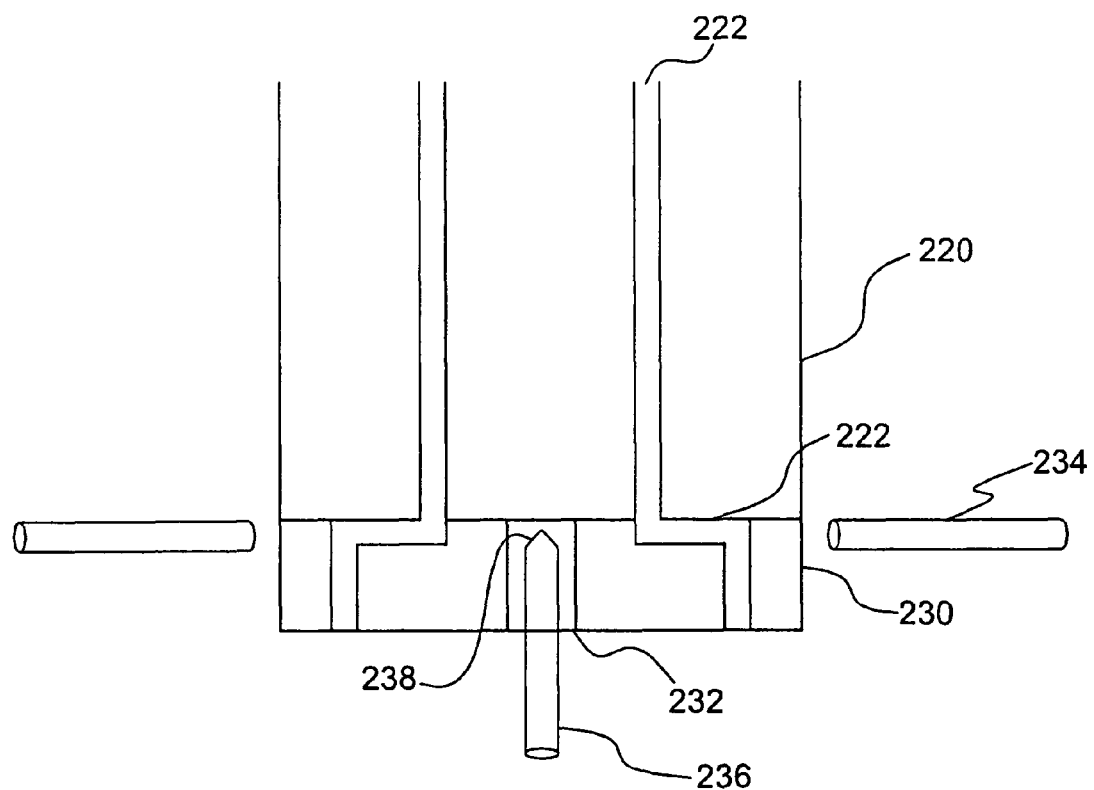
FIG. 16 shows an example of a drawn microchanel array forming a diagnostic device according to the present invention.

FIG. 16 shows a drawn substrate 220 having two drawn channels 222. Attached to one end of the drawn substrate 220 is an end cap substrate 230. The end cap contains extensions of the two channels 222, a central hole 232, and may be fused or otherwise adhered to the drawn substrate 220. Two detector fibers 234 are disposed on either side of the end cap 230 to accept light signals from the sides of the end cap 230. A source fiber 236, having an emitter tip 238, is used to input light signals into the end cap 230 through the central hole 232. The channels 222 as shown are primarily disposed along a direction parallel to the array 220. However, portions of the channels 222 in the end cap 230 extend in a direction perpendicular to the primary direction. These portions can serve, for example, to increase the overall length of the channels, or to increase the optical path length through which light emitted from the emitter tip 238 must pass before being accepted by the detector fibers 234. This may be useful when the analyte being detected is only weakly interacting with the light signals due to low reactivity, low density, low concentration, low absorptivity, or other factors.

Figure 17:
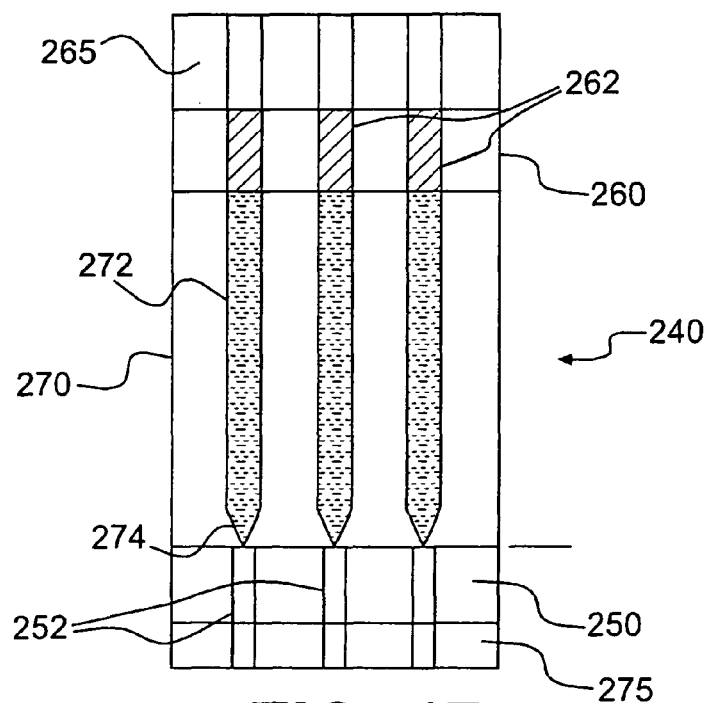
FIG. 17 shows an example of a capillary electrochromatography device according to the present invention.

Referring now to FIG. 17, a micro channel array device 240 for capillary electrochromatography is made up of four end caps substrates 250, 260, 265, 275 and a drawn substrate 270. The first end cap substrate 265 is an injector cap similar to that shown in FIG. 5a-e which interfaces the device to the analytical instrument. The second end cap substrate 260 is a filter section end cap and likewise includes three endcap channels 262 and may be made by drawing. Additionally, filter material is disposed within the endcap channels 262. The third endcap substrate 250 is a detector section. The detector section 250 includes three endcap channels 252 and is preferably made by drawing as described above. The fourth end cap substrate 275 is an outlet interface similar to that shown in FIG. 5a-e which interfaces the device to the analytical instrument. The micro channel array 270 has three drawn channels 272 which are aligned on one end with the filter ports 262, and on the other end with the detector ports 252 so that they may be in fluidic communication. The drawn channels 272 form the electrochromatography columns through which an analyte will pass during analysis. As depicted in FIG. 17 the drawn channels are filled with a chromatographic media that is known to those skilled in the art. As illustrated, the channels 272 may also have tapered ends 274 leading to the detector section 250. These tapered ends may be formed by varying the draw speed of the preform body during manufacture or by micromachining techniques as described earlier. The tapered ends 274 serve to retain the aforementioned chromatographic media in the drawn substrate. The tapered ends 274 may be placed in the third endcap 250 to serve the same purpose.

Figure 18:
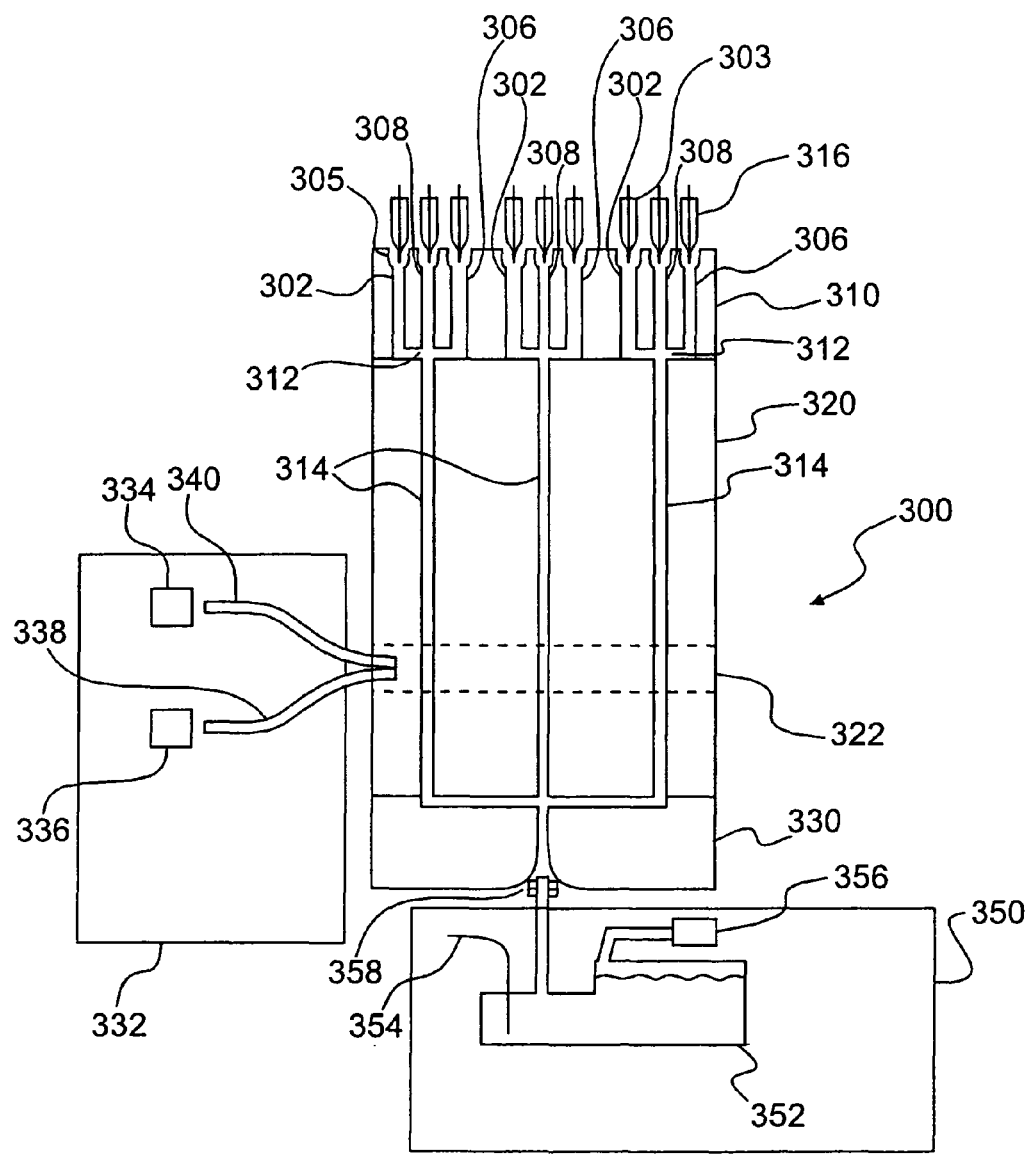
FIG. 18 is a schematic diagram of a micro capillary array device according to the present invention.

FIG. 18 shows a completed micro capillary array device 300 as could be used in a lab on a chip application. The device 300 includes an insertion endcap substrate 310, a drawn substrate 320, and an outlet endcap substrate 330. The insertion endcap substrate 310 serves as an interface to the instrument which dispenses the analyte and buffer, contains reservoirs 302 for the analyte, buffer 308 and analyte waste 306, and contains the valve 312 for dispensing the analyte into the drawn channels 314. Inlet electrodes 303 are positioned at entrances to the inlets and the inlet ports 305 are flared. The drawn substrate 320 serves two functions in this example: analyte separation and detection. The outlet endcap 330 substrate acts to route buffer and analyte into an interface with the analytical instrument.

An example of a process of analyzing the analyte using the device 300 shown in FIG. 18 can be described as follows: Buffer and analyte are dispensed into the reservoirs 302, 308 of the insertion endcap substrate via a 96 or 384 well plate fluid dispenser 316, for example, as is common in the industry. This 96 well plate fluid dispensing technology can be modified to incorporate the inlet electrodes 303 required for applying the electrical fields discussed herein. Initially all device conduits are filled with buffer via differential pressure across the device 300. Then the analyte is dispensed into the analyte reservoir 302 of the insertion endcap substrate 310 in preparation for injection. An electric field across the analyte reservoir and analyte waste reservoir draws a portion of the analyte into the valve region 312. This provides an injection of analyte into the separation pathway 314. Then an electric field is applied between the buffer reservoir 308 and the buffer waste reservoir 352 which initiates an electrophoretic separation of the analyte in the drawn channel 314. As the analyte migrates down the drawn channel 314 it passes through the detection section 322 allowing for quantification by spectrophotometric techniques. An interface between the drawn substrate detection section 322 and the spectrophotometric instrument 332 is accomplished in this example through an excitation optical fiber 338 (which guide light from a light source 336 into the drawn channel 314) and an emission optical fiber 340 (which guides light output from the drawn channel to the detector 334). The analyzed materials and buffer then proceed into the outlet endcap substrate 330 which interfaces with the analytical instrument 350. This interface includes a buffer waste reservoir 352, an outlet electrode 354, a differential pressure device 356 (such as a vacuum) as a means of initially filling or subsequently rinsing all conduits, and a mechanism 358 providing a sealed connection into the outlet endcap substrate 330. Components of this interface may be integral to the outlet endcap substrate 330 itself.

Figure 19A:
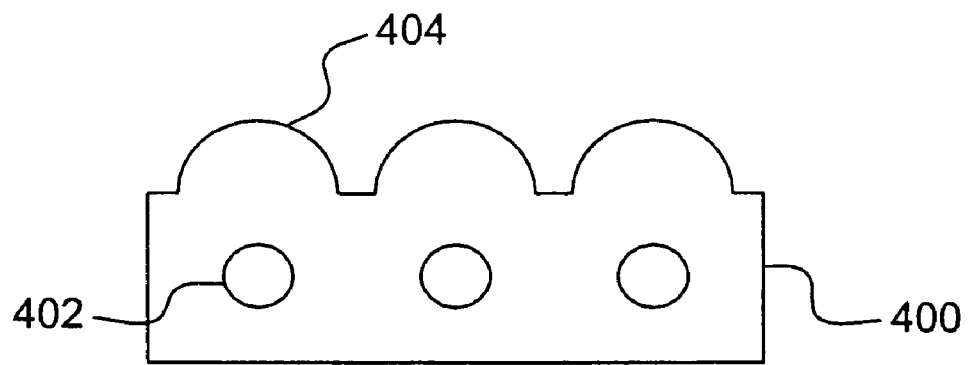
FIGS. 19a and 19b are schematic cross sections of drawn array devices according to the present invention.
Figure 19B:
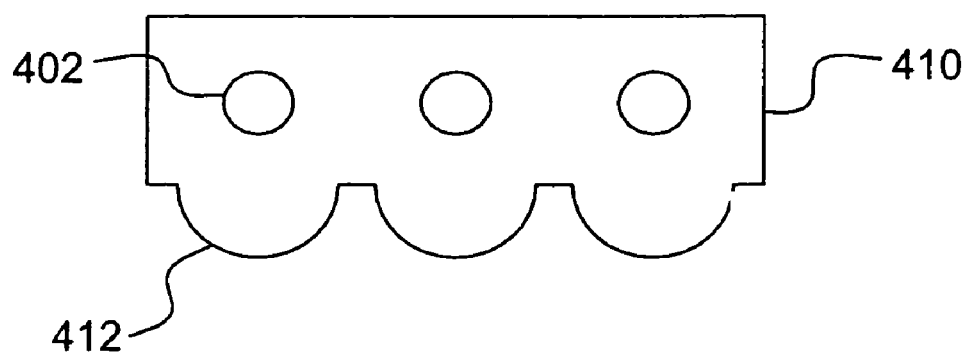

FIG. 19a and FIG. 19b each show partial cross sections of drawn array devices according to the present invention. FIG. 19a illustrates a drawn array 400 which contains a plurality of drawn channels 402 and a corresponding plurality of lenses 404 formed in the array. The lenses 404 can be used, for example, to focus interrogating light onto the drawn channels for illuminating them, for inducing fluorescence, or other purposes known to those of skill in related arts. The drawn array 400 can be formed as the previously discussed arrays, by drawing a preform in the shape of the final array.

FIG. 19b shows a drawn array 410 similar to the drawn array 400. Rather than including lenses, however, a curved portion including a reflective surface 412 is formed in the drawn array 410. The curved, reflective portion 412 can be used, for example, to focus light on the channel. Though the curved portion is shown to be semicircular, it may likewise be hyperbolic to better focus light on the focal point. For further improvement, the two concepts may be used together so that lenses are formed on upper (for example) surfaces while reflectors are formed on lower surfaces. In this way, the light may be used with great efficiency.

While the invention has been described in connection with what are presently considered to be the most practical and preferred embodiments, it is to be understood that the invention is not limited to the disclosed embodiments, but on the contrary it is intended to cover various modifications and equivalent arrangements included within the spirit and scope of the claims which follow.

What is claimed is:

1. A method of making a device for analyzing a plurality of sample components, comprising, in order:
    forming at least two hollow channels in a preform substrate along a length of said preform substrate;
    heating said preform substrate including said at least two hollow channels; and
    drawing said preform substrate along said length so as to extend a length of said at least two hollow channels while substantially maintaining a cross sectional geometry of said at least two hollow channels, wherein a cross-sectional area of at least one of the at least two hollow channels is in the range of 0.0001 mm$^2$ to 1 mm$^2$ after said drawing.

2. The method of claim 1, wherein the length of at least one of said at least two hollow channels after said drawing is in the range of 1 mm to 1 km.

3. The method of claim 1, wherein, subsequently to said drawing, the preform substrate is utilized in a micro electro mechanical system.

4. The method of claim 1, wherein, subsequently to said drawing, the preform substrate is utilized in a lab on a chip system.

5. The method of claim 1, further comprising adjusting one or more of draw rate, draw tensions, draw temperature, and draw pressure to vary a cross-sectional area of said at least two hollow channels along the length of said preform.

6. The method of claim 1, wherein said preform substrate includes an optical waveguide formed therein and extending in a direction parallel to the length of said preform.

7. (The method of claim 1, wherein said preform substrate further comprises an electrical conductor extending in the direction parallel to the length of said preform.

8. The method of claim 1, wherein the preform substrate further comprises at least one optical isolator extending in the direction parallel to the length of said preform.

9. The method of claim 1, wherein the cross-sectional geometry of a first one of the at least two hollow channels after said drawing is different from the cross-sectional geometry of a second one of the at least two drawn channels.

10. The method of claim 1, wherein the preform substrate comprises a material selected from the group comprising: glass, ceramic, and thermoplastic polymers.

11. The method of claim 1, wherein the preform substrate comprises a material selected from the group comprising: fused silica, fused quartz, and PMMA.

12. The method of claim 1, further comprising providing the preform substrate with an exterior coating comprising a material selected from the group consisting of polyimide, acrylate, fluorinated acrylate, silicone, metal, and optical cladding.

13. The method of claim 1, further comprising, after said drawing, providing the drawn preformsubstrate with an exterior coating comprising a material selected from the group consisting of magnetic, radio opaque, optically filtering, conductive, and dielectric.

14. The method of claim 1, further comprising providing the preform substrate with an interior coating comprising a material selected from the group consisting of hydrophobic bonded phases, hydrophyllic bonded phases, polyacrlyarnides, silver, silver halide, gold, and polytetrafluoroethylene.

15. The method of claim 1, wherein at least a selected one of the at least two hollow channels after said drawing has at least of a portion of a wall comprising a lens.

16. The method of claim 1, wherein at least a selected one of the at least two hollow channels after said drawing has at least a portion of a wall comprising a reflector.

17. The method of claim 1, wherein the preform substrate after said drawing has at least one alignment groove on its exterior surface, down its length.

18. The method of claim 1, wherein said preform substrate further includes an optical fiber interfaced into one of the hollow channels.

19. The method of claim 18, wherein said preform substrate further includes a structure for redirecting light in the hollow channel interfaced with the optical fiber.

20. The method of claim 19, wherein the structure for redirecting light comprises a reflecting surface located on the end of the optical fiber interfaced into the hollow channel.

21. The method of claim 20, wherein after said drawing the at least two hollow channels have a substantially constant spacing therebetween, a substantially constant relative rotational alignment and a substantially constant relative angular alignment along the length of the substrate.

22. The method of claim 20, wherein two of the hollow channels after said drawing have a portion of a wall comprising a lens and the two lenses have a substantially constant spacing therebetween, a substantially constant relative rotational alignment and a substantially constant relative angular alignment along the length of the substrate.

23. The method of claim 1, further comprising cutting said perform substrate after said drawing to a desired length.

24. The method of claim 1, further comprising attaching at least one endcap substrate having at least one endcap channel to said preform substrate after said drawing, said at least one endcap channel being in fluid communication with at least one hollow channel.

25. The method of claim 24, wherein said endcap channel is in fluid communication with said at least two hollow channels.

26. The method of claim 24, wherein said attaching comprises heating said endcap substrate and drawing said endcap substrate so as to extend a length of said at least one endcap channel while substantially maintaining a cross sectional geometry of said at least one endcap channel.

27. The method of claim 24, wherein said endcap substrate comprises an endcap channel having a cross-sectional geometry different from a cross-sectional geometry of the at least one endcap channel.

28. The method of claim 24, wherein said at least one endcap channel has at least a portion of a wall comprising a lens.

29. The method of claim 24, wherein said at least one endcap channel has at least a portion of a wall comprising a reflector.

30. The method of claim 24, wherein said at least one endcap substrate has at least one alignment groove on its exterior surface.

31. The method of claim 24, wherein another endcap channel and said at least one endcap channel have a substantially constant spacing therebetween, a substantially constant relative rotational alignment and a substantially constant relative angular alignment along a length of the endcap substrate.

32. The method of claim 1, wherein forming said at least two hollow channels comprises machining the preform substrate.

33. The method of claim 1, wherein forming said at least two hollow channels comprises etching the preform substrate.

* * * * *